US008728393B2

(12) United States Patent
Knott et al.

(10) Patent No.: US 8,728,393 B2
(45) Date of Patent: May 20, 2014

(54) APPARATUS AND METHOD OF STERILIZING INNER WALLS OF CONTAINERS WITH A REFLECTOR APPARATUS

(71) Applicant: Krones AG, Neutraubling (DE)

(72) Inventors: Josef Knott, Walkenstetten/Schierling (DE); Jochen Krueger, Hagelstadt (DE)

(73) Assignee: Krones AG (DE)

( * ) Notice: Subject to any disclaimer, the term of this patent is extended or adjusted under 35 U.S.C. 154(b) by 0 days.

(21) Appl. No.: 13/706,121

(22) Filed: Dec. 5, 2012

(65) Prior Publication Data

US 2013/0149193 A1    Jun. 13, 2013

(30) Foreign Application Priority Data

Dec. 8, 2011    (DE) .......................... 10 2011 056 162

(51) Int. Cl.
| | | |
|---|---|---|
| *A61L 2/00* | (2006.01) | |
| *B01J 19/08* | (2006.01) | |
| *G01N 21/00* | (2006.01) | |
| *A23B 4/16* | (2006.01) | |
| *B65B 25/06* | (2006.01) | |
| *B65D 81/20* | (2006.01) | |
| *B65D 81/26* | (2006.01) | |
| *A23L 1/31* | (2006.01) | |
| *A01N 1/02* | (2006.01) | |
| *A61L 9/18* | (2006.01) | |
| *A61L 12/00* | (2006.01) | |

(52) U.S. Cl.
CPC ............... *A23B 4/16* (2013.01); *B65B 25/067* (2013.01); *B65D 81/2076* (2013.01); *B65D 81/264* (2013.01); *A23L 1/31* (2013.01); *A01N 1/0294* (2013.01); *A61L 2/00* (2013.01); *A61L 9/18* (2013.01); *A61L 12/00* (2013.01)
USPC ......... 422/22; 422/1; 422/186.05; 422/186.3; 250/453.11; 250/455.11; 250/492.1; 99/451; 134/1

(58) Field of Classification Search
CPC .... A23B 4/16; B65B 25/067; B65D 81/2076; B65D 81/264; A23L 1/31; A01N 1/0294; A61L 2/00; A61L 9/18; A61L 12/00
USPC ................ 422/1, 20, 21–22, 24, 186, 186.05, 422/186.3, 187; 250/453.11, 455.11, 492.1; 99/451; 134/1
See application file for complete search history.

(56) References Cited

U.S. PATENT DOCUMENTS

| | | | |
|---|---|---|---|
| 6,509,127 B1 | 1/2003 | Yamashita | ...................... 430/30 |
| 2007/0283667 A1 | 12/2007 | Kristiansson et al. | .......... 53/426 |

(Continued)

FOREIGN PATENT DOCUMENTS

| | | | |
|---|---|---|---|
| DE | CH611847 | 6/1979 | ............. B65B 55/08 |
| DE | 102008045187 | 3/2010 | ................ A61L 2/08 |

(Continued)

OTHER PUBLICATIONS

European Search Report issued in parallel European Application Serial No. 12 19 4888 dated Mar. 4, 2013 (2 pgs).

(Continued)

*Primary Examiner* — Monzer R Chorbaji
(74) *Attorney, Agent, or Firm* — Hayes Soloway P.C.

(57) ABSTRACT

An apparatus and a method of sterilizing inner walls of containers, wherein the apparatus has at least one electron beam emitter with at least one electron beam accelerator and an outlet window for the electron beams, a conveying device for conveying the containers to be sterilized and a reciprocating device for permitting a relative movement between the containers and the outlet window in a longitudinal direction of the containers. A reflector apparatus is connected to the electron beam emitter in a positively locking and/or friction locking manner at least locally in a region of the outlet window and is capable of being introduced at least locally during a defined period of time into an interior space of the container to be sterilized, in order to apply the electron beams to the inner walls of the container.

22 Claims, 2 Drawing Sheets

(56) References Cited

U.S. PATENT DOCUMENTS

| | | |
|---|---|---|
| 2010/0054987 A1 | 3/2010 | Krueger et al. .................. 422/3 |
| 2010/0209290 A1* | 8/2010 | Cirri et al. ...................... 422/22 |
| 2010/0247373 A1 | 9/2010 | Avnery ........................... 422/22 |

FOREIGN PATENT DOCUMENTS

| | | | |
|---|---|---|---|
| DE | 102008054110 | 5/2010 | ............... A61L 2/08 |
| EP | 2 161 202 | 3/2010 | ............... A61L 2/08 |
| WO | WO 2007/095205 | 8/2007 | |
| WO | WO 2008/129397 | 10/2008 | |
| WO | WO2010049150 | 5/2010 | ............... A61L 2/08 |

OTHER PUBLICATIONS

German Search Report issued for corresponding application No. 10 2011 056 162.5, dated Aug. 30, 2012 (5 pgs).

* cited by examiner

APPARATUS AND METHOD OF STERILIZING INNER WALLS OF CONTAINERS WITH A REFLECTOR APPARATUS

BACKGROUND OF THE INVENTION

The present invention relates to an apparatus and to a method of sterilizing inner walls of containers with at least one electron beam emitter.

Apparatus for the sterilization of containers are incorporated for example in production and filling plants of container and bottle manufacturers, in order preferably to permit a sterilization of the interior space of the containers which is brought into contact with the medium to be received in the container.

A sterilization of the containers can be carried out in this case by means of different methods. In this way for example, a liquid or flowable sterilization agent (chemical sterilization) can be applied to the inner wall of the container or the container can be immersed in an agent of this type, in which case, however, the container usually still has to be rinsed and dried after the sterilization in order to prevent a negative interaction between the sterilization agent and the filled medium.

Steam or hot air sterilization, i.e. the sterilization by heating, is likewise known, in which case, however, the containers to be sterilized have to be heated to extremely high temperatures in order to permit a substantially complete sterilization of the containers by destruction of the bacteria. This could also lead to the deformation of and long-term damage to the containers to be sterilized, so that a method of this type cannot be used, in particular in the region of the production of plastics material containers.

Sterilization by means of radiation is also a method which is preferably used in the case of containers already expanded into their final shape, in order to achieve a complete sterilization in this way. Electron beams which are emitted by an electron beam emitter and which are introduced into the interior space of the container are preferably used as the radiation in this case.

In this way for example, DE 10 2008 045 187 A1 also discloses a method of sterilizing containers, in which a treatment head is introduced into the interior of the blow-moulded bottle, emits radiation and applies it to the internal surface of the bottle. This treatment head or radiation finger is designed in its construction in such a way that it is possible to sterilize containers such as bottles etc. which are already expanded into their final size and shape and which, in addition, have at least one defined bottle aperture diameter and a defined wall diameter in order to allow the treatment head or the distal end thereof to penetrate into the interior of the container and to irradiate the internal surface over the complete periphery for sterilization purposes.

On account of their function, however, treatment heads of this type have a minimum external diameter of approximately 16 mm and, in this way, although they can be inserted through the majority of container apertures, they cannot be inserted into conventional pre-forms since the internal diameter of these pre-forms is reduced with respect to the distal end, as viewed from the aperture.

This means that, if—instead of sterilizing or irradiating already completely shaped-out containers or bottles—pre-forms are preferably to be irradiated and thus sterilized, when a treatment head of this type is used and introduced into the aperture area of the pre-form just behind the aperture thereof a very large radiation dosage would strike the surface of the interior space of the container, whereas in contrast an excessively small radiation dosage would be applied to the internal surface of the distal end, i.e. the lower closed end, of the pre-form, as a result of which a reliable sterilization over the entire periphery of the inner wall of the pre-form would no longer take place.

Accordingly, the object of the present invention is to make available an apparatus and a method of sterilizing inner walls of containers and, in particular, of pre-forms, which shadows areas of the container not to be sterilized, and the radiation striking the aperture area in an over-metered manner is transmitted to the lower distal areas of the container in such a way that it is consequently possible to ensure a substantially uniform irradiation of the entire interior space of the container.

SUMMARY OF THE INVENTION

Consequently an apparatus for the sterilization of inner walls of containers with at least one electron beam emitter with at least one electron beam accelerator and with an outlet window for the electron beams, a conveying device for conveying the containers to be sterilized and a reciprocating device for permitting a relative movement between the containers and the outlet window in a longitudinal direction of the containers, is claimed.

This apparatus according to the invention additionally has a reflector apparatus which is connected to the electron beam emitter in a positively locking and/or friction locking manner at least locally in a region of the outlet window and which is capable of being introduced at least locally during a defined period of time into an interior space of the container to be sterilized, in order to apply the electron beams to the inner walls of the container. It is preferable for the reflector apparatus to be connected to the electron beam emitter in a detachable manner.

As is known from the general prior art, in the case of an electron beam emitter the electrons are emitted by a suitable cathode and are accelerated to an anode by a constant electrical potential difference. The release of the electrons present in the cathode material is carried out either by the process of thermionic emission (Edison effect), of field emission or even of photoemission (external photoelectric effect).

The emitted or generated electron beams are thus, accelerated by the electron beam accelerator, discharged to the environment by way of a suitable outlet window, so as subsequently to be able to strike an object to be irradiated accordingly. This means that the electrons are accelerated as an electron beam out of a vacuum chamber through an outlet window, the outlet window usually being formed by a metallic foil. This metallic foil of the outlet window is generally formed by a material of high strength, such as for example of titanium in order to withstand the difference in pressure between the interior and the outside of the vacuum chamber.

As well as the sterilization device which has inter alia the electron beam emitter, the apparatus according to the invention likewise has a conveying device for conveying the containers through the sterilization area of the plant as a whole which is used for the manufacture, expansion, sterilization, filling and closure of the containers. This conveying device or these conveying devices can have for example conveying star wheels, conveying worms and/or conveyor belts etc. with suitable gripping elements for gripping the containers in the aperture area or carrier elements for carrying the containers in the base area.

A further unit of the apparatus according to the invention is a reciprocating device which either moves the containers to be sterilized from the conveying device thereof in the direction of the sterilization device and thus in the direction of the electron beam emitter and the outlet window thereof or which moves the aforesaid sterilization device and the electron beam emitter respectively in the direction of the container to be sterilized. In this case the containers or even the sterilization device are moved substantially in the longitudinal direction. of the containers, i.e. in the vertical direction. As a result of this, the sterilization device or the electron beam emitter respectively performs a relative movement towards the containers or away from the containers or the containers also perform a relative movement towards the sterilization device or the electron beam emitter or away from the latter respectively.

It is also possible, however, for both the containers and the sterilization device or elements of the sterilization device respectively, such as for example the electron beam emitter, to be moved substantially to one another so that the two elements, i.e. both the sterilization device or the electron beam emitter respectively and also the containers jointly perform a relative movement to one another.

It is preferable if the containers to be sterilized are pre-forms, the internal diameter of which is substantially smaller in the lower region, i.e. the region opposite the aperture area, than in the aperture area. This means that the diameter of the pre-form tapers substantially at least locally starting from the aperture area.

In order to be able to introduce the beams emitted by the electron beam emitter into the inner region of the container in such a way that the emitted beams can strike the internal surface of the container in a substantially directed manner, in order to be able to sterilize preferably the entire internal surface completely as a result, use is made of a reflector apparatus according to the invention or a collimator or a collimator tube respectively, which is connected in a positively locking and/or friction-locking manner to the electron beam emitter, in particular in the region of the outlet window, in order to be able substantially to absorb or collect the electron radiation and to be able to guide or convey it in the direction of the interior space of the container.

A connection with positive locking between the reflector apparatus and the electron beam emitter can be made possible for example by means of suitable holding apparatus, such as projections engaging in grooves, in which case for example the outside of the electron beam emitter has grooves or indentations or recesses respectively into which projections or stubs etc. respectively of the reflector apparatus can engage. In contrast, it is also possible for the reflector apparatus to have grooves and for the electron beam emitter to have projections which engage one in the other.

In addition, a screw fastening between the electron beam emitter and the reflector apparatus is possible, in which case for example the electron beam emitter has an external thread onto which an internal thread cut on or rolled onto the reflector apparatus can be screwed.

A connection with positive locking between the electron beam emitter and the reflector apparatus can be produced for example by a compression bond by at least one portion, i.e. an end portion, of the reflector apparatus being turned or pressed over the periphery of a portion of the electron beam emitter in which the outlet window is preferably arranged. To this end, at least this one portion of the reflector apparatus has a material which is resiliently deformable essentially at least to a slight degree and which first of all can be turned easily in order to be able to be pressed over the portion of the electron beam emitter and is then restored again to its original state, which ensures that one portion of the reflector apparatus is pressed against one portion of the electron beam emitter.

It is also possible for the connection between the electron beam emitter and the reflector apparatus to be made both in a positively locking manner and in a friction locking manner, in order to prevent an undesired release of the reflector apparatus from the electron beam emitter.

It is preferable for the connection with positive locking and/or friction locking to be capable of being released at any time, so that if necessary the reflector apparatus can be removed from the electron beam emitter and can be replaced with another reflector apparatus with a smaller or larger internal diameter for example. Consequently it is possible for reflector apparatus of the most widely differing designs (fittings) to be able to be used for the containers or pre-forms of the most widely differing designs.

This reflector apparatus or reflector device respectively can consequently be introduced into the interior space of the container during the transmission of the electron radiation by the electron beam emitter in the direction of the interior space of the container itself, for example by the reflector apparatus being moved by the reciprocating device in a substantially vertical direction towards the container or by the container to be sterilized being moved by the reciprocating device in a substantially vertical direction towards the reflector apparatus. In this way, it is also possible that the containers to be sterilized are moved one upon the other by the reciprocating device in exactly the same way as the reflector apparatus in a substantially vertical direction which corresponds to the longitudinal direction of the containers.

In this case the electron beams emitted by the electron beam emitter are guided through the reflector apparatus substantially in such a way that the radiation can be applied in a directed manner, i.e. in a substantially defined manner and in a defined radiation metering, i.e. quantity, to the internal surface of the container to be sterilized.

Consequently the present invention also relates to a reflector apparatus which reflects the electrons emitted by an electron beam emitter at least once on its internal surface—which preferably has a material with a large nucleus mass—and bundles them to form bundled electron radiation with a small diameter and a low degree of scatter and consequently discharges them in a substantially directed manner onto the inner wall of a body and preferably a container.

It is preferable for a reflector apparatus of this type to be in the form of a tube and to have at least one first opening for the admittance of the electron beams into the reflector apparatus and one second opening for the outlet of the electron beams into the interior space of the containers to be sterilized as well as an internal surface for reflecting and/or bundling the electron beams. It is preferable for a cross-section of the second opening to be smaller than a cross-section of the first opening. It is preferable for the reflector apparatus to have a circular cross-section.

This means that at least the internal surface of the reflector apparatus preferably has at least in part a material with a large nucleus mass or a high nucleus charge number respectively, in order to reflect the electron beams on the internal surface thereof substantially completely and preferably also to bundle them, in order to be able to apply bundled electron beams in a defined or directed manner by the reflection thereof onto the internal surface of the container to be sterilized. Consequently an undesired absorption of the electron beams should be substantially prevented by the use of a material of this type.

In this case the material, which should have at least in part a large nucleus mass, is preferably selected from a group comprising tungsten, tantalum, platinum, gold and/or materials with comparable chemical and physical properties.

By way of example, on gold surfaces for electrons in the 100 keV range, degrees of reflection of up to 50% in the case of vertical incidence and up to 70% in the case of grazing incidence of the electrodes onto the reflecting surface can be achieved.

It is consequently advantageous for it to be possible for the electrons to be steered or reflected in a defined direction and to be bundled to a radiation diameter scattering to a substantially low degree.

In an advantageous manner the internal surface of the reflector apparatus has no edge areas or steps or grooves etc. respectively, so that the radiation can be reflected in a defined manner in the direction of the interior space of the container to be sterilized, without being deflected in an undesired manner.

In a preferred embodiment at least one first portion of the reflector apparatus, which is capable of being introduced into the interior space of the container, has a smaller diameter than a second portion of the reflector apparatus, which is connected to the electron beam emitter.

This is advantageous since the electron beam emitter usually has an outlet window for the discharge of the electron beams, which is larger in diameter than the interior space of the container to be sterilized.

As a result, a transition region should be formed in an advantageous manner between the opening of the reflector apparatus, which is connected to the electron beam emitter, and the opening of the reflector apparatus, which is capable of being introduced into the interior space of the container to be sterilized, so that in the first place the emitted electron beams are completely received in the reflector apparatus and are transmitted inside the latter and consequently are applied substantially completely to the surface of the container to be sterilized, without electron beams being screened out or deflected from the surface to be sterilized. This means that a high degree of efficiency of the sterilization device may be achieved by means of the reflector apparatus.

Consequently it is preferable for at least one third portion of the reflector apparatus, as viewed in the direction of the first portion starting from the second portion, to have a region which tapers in diameter.

This means that the transition region between the first opening and the second opening of the reflector apparatus has a portion which tapers in diameter in order to permit a complete penetration into the interior space of the container through the reflector apparatus or at least a corresponding region of this reflector apparatus.

In a further preferred embodiment the reflector apparatus is used for guiding a tempering air flow for tempering and preferably for cooling the container at least during the sterilization procedure.

Consequently a tempering apparatus for tempering the containers to be sterilized is preferably activated at least during the sterilization procedure in such a way that it discharges a tempering air flow in the direction of the containers.

This tempering air flow is preferably used for cooling the foil of the electron outlet window of the electron beam emitter, the tempering air flow preferably being set in its through-flow quantity in such a way that after passing the outlet window the air is heated to a defined temperature on account of the thermal radiation discharged by the outlet window, in which case it is preferable for the aforesaid tempering air flow additionally to allow the container to be heated or to be kept warm.

It would also be possible, however, for the tempering air flow to leave the tempering apparatus when heated beforehand to a defined temperature, in which case the temperature of the tempering air flow is set in such a way that cooling of the outlet window and thus a tempering of the container can consequently be made possible.

This means that the tempering apparatus is arranged for example in the region of the sterilization apparatus and preferably in the region of the electron beam emitter in order to introduce the tempering air flow for example by way of the outlet window through the reflector apparatus into the interior space of the container to be sterilized.

In addition, a method of sterilizing inner walls of a container by means of electron beams discharged by an electron beam emitter is claimed.

In accordance with the method according to the invention a reflector apparatus—connected in a region of an outlet window of the electron beams in a positively locking and/or friction locking manner to the electron beam emitter—for reflecting and/or bundling the electron beams is introduced at least locally during a defined period of time into an interior space of the container to be sterilized, in order to apply the electron beams to the inner walls of the container.

In accordance with a preferred embodiment the reflector apparatus reflects at least one of the electron beams emitted by the electron beam emitter at least once after the exit thereof out of the electron beam emitter by way of an internal surface having at least in part a material with a large nucleus mass.

Consequently the electrons are preferably reflected substantially completely on the inner surface and are bundled to form an electron beam with a low degree of scatter and with an essentially small diameter, in order to be applied in a directed manner to the internal surface of the container to be sterilized.

This means that the interior space of containers and, in particular, of pre-forms is sterilized preferably by means of the reflector apparatus by the application of electron beams reflected and bundled on an internal surface of the reflector apparatus.

To this end it is preferable, as already described above, for the reflector apparatus and/or the containers to be moved during a defined period of time at least for a time at a relative movement velocity in a longitudinal direction of the containers by means of a reciprocating device in order to permit a relative movement between the containers and the reflector apparatus. This means that either the reflector apparatus is moved by means of the reciprocating device in the direction of the containers to be sterilized and/or the containers to be sterilized are moved by means of the reciprocating device in the direction of the reflector apparatus.

Further advantages, aims and properties of the present invention are explained with reference to the following description of accompanying drawings, in which an embodiment of a reflector apparatus of an apparatus according to the invention for the sterilization of an interior space of containers is illustrated by way of example.

BRIEF DESCRIPTION OF THE DRAWINGS

Components which correspond at least substantially with respect to their function in the figures can be designated with the same references in this case, it being unnecessary for these components to be designated and explained in all the figures. In the figures

DETAILED DESCRIPTION OF THE INVENTION

Figure 1:
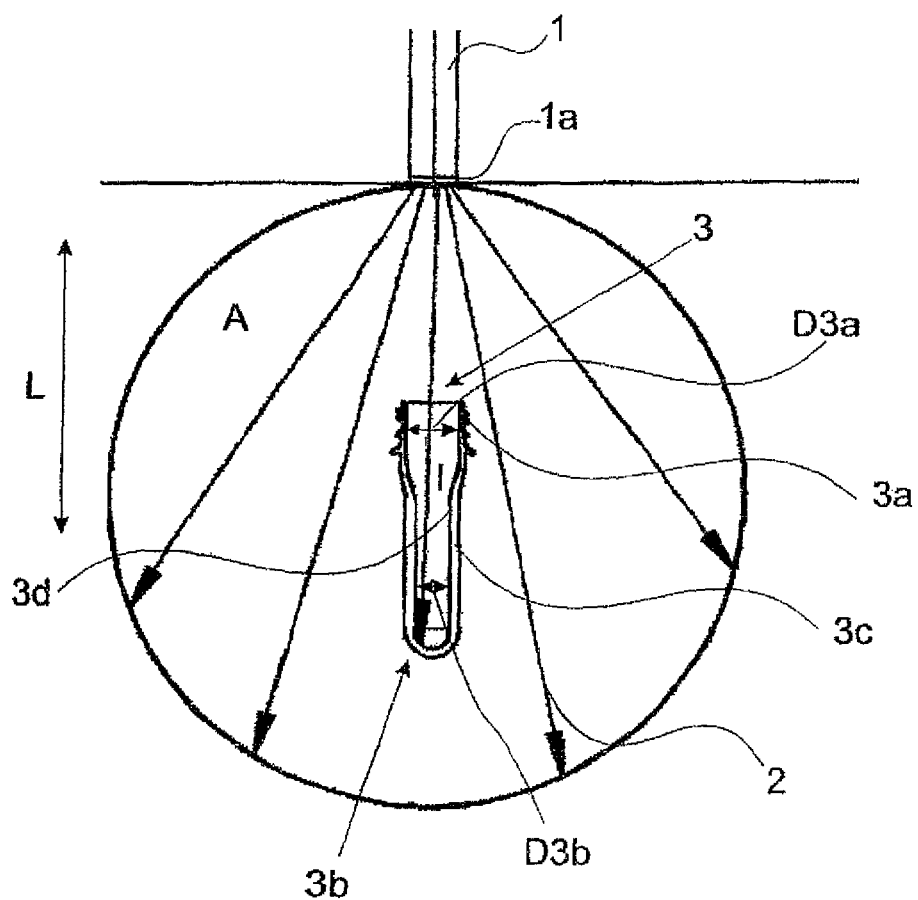
FIG. 1 is a basic drawing of a sterilization apparatus known from the prior art for the sterilization of containers by means of electron beams as well as an embodiment of a pre-form and the striking of the electron beams against this pre-form.

FIG. 1 is a basic drawing of a sterilization apparatus 1 or an electron beam emitter 1 known from the prior art for the sterilization of containers by means of electron beams 2 as well as an embodiment of a pre-form 3 and the striking of the electron beams 2 against this pre-form 3.

The illustrated embodiment of the pre-form 3 has a diameter D3a or internal diameter D3a respectively in the aperture area 3a which is larger than the diameter D3b or internal diameter D3b respectively of the lower area 3b, so that a complete sterilization at least of the lower area 3b of the pre-form 3, as already explained above, would take place by means of a radiation finger known from the known prior art.

Without a suitable apparatus such as the reflector apparatus, the electron beams 2 emitted by the electron beam emitter 1 can issue only in a non-directed manner out of the outlet window 1a and consequently arrive in part in the inner region I or the interior space I of the pre-form 3 or not at all. The emitted electron radiation 2 is consequently also discharged into the external environment A of the pre-form 3 and is accordingly no longer used for the sterilization of the internal surface 3d of the wall 3c of the pre-form 3. The radiation 2 is consequently unused and lost, as a result of which additional costs arise.

In addition, it is consequently not possible to ensure sterilization over the entire periphery of the inner wall 3d of the pre-form 3 by the electron radiation 2, since it is not possible to predict precisely where the electron beams 2 will strike.

Figure 2:
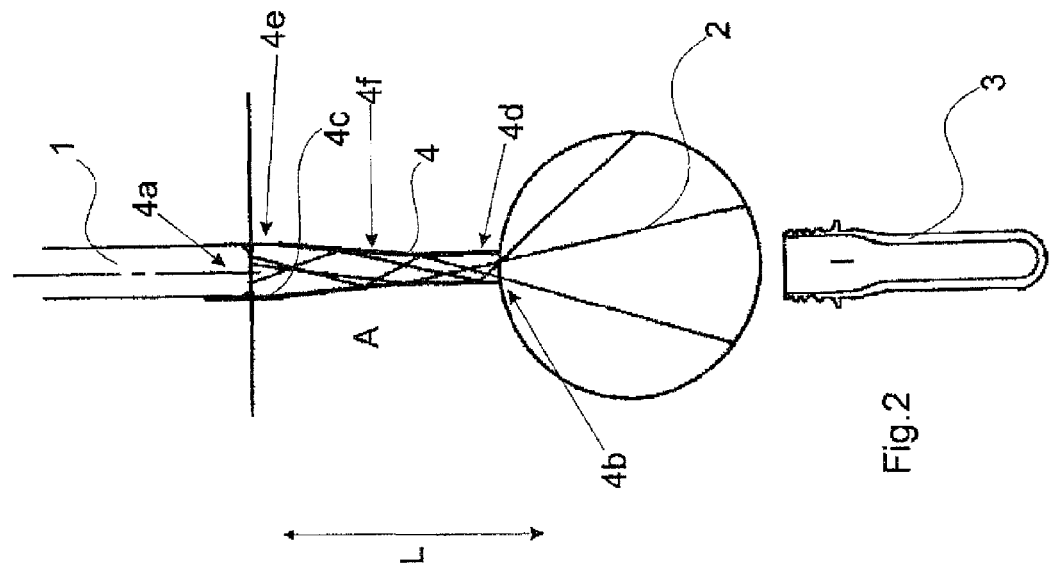
FIG. 2 is a basic drawing of an embodiment of a reflector apparatus of the apparatus according to the invention for the sterilization of an interior space of containers in a position situated outside an embodiment of a pre-form.

In order substantially to bundle the electron radiation 2 and to be able to apply it in a directed manner onto the internal surface 3d of the wall 3c or the inner wall 3c of the pre-form 3 respectively, use is made according to the invention of a reflector apparatus 4 which in accordance with an embodiment is illustrated in FIG. 2 in the form of a basic drawing in a position situated outside an embodiment of a pre-form 3.

The reflector apparatus 4 has a first opening 4a in a second portion 4e of the reflector apparatus 4, which is connected to the electron beam emitter 1 and, in particular, to the outlet window 1a of the electron beam emitter 1 in such a way that the electron beams 2 emitted by the electron beam emitter 1 can pass by way of this first opening 4a into the reflector apparatus 4, in order to be conveyed or transmitted by the reflector apparatus 4 in the direction towards the second opening 4b which is situated on a first portion 4d of the reflector apparatus 4 capable of being introduced into the pre-form 3.

This transmission is carried out by way of a reflection of the electron beams 2 on the internal surface 4c of the reflector apparatus 4. In addition, the electron beams 2 are not only reflected substantially completely by this internal surface 4c, which preferably has at least in part a material with a large nucleus mass, but are also bundled into beams of small diameter. An undesired scattering of the electron beams 2 should therefore be prevented as far as possible.

In order to allow the first portion 4d of the reflector apparatus 4 to be introduced into the interior space I of the pre-form 3, the diameter of the first portion 4d of the reflector apparatus 4 is made substantially smaller or shorter respectively than the diameter of the second portion 4e, which is preferably made larger than the diameter of the first portion 4d in order to allow a connection in a positively locking and/or friction locking manner to the electron beam emitter 1 in such a way that the reflector apparatus 4 for example is turned over the electron beam emitter 1 substantially at least locally and thus completely surrounds a portion of the electron beam emitter on the periphery thereof. As a result, the electron beams 2 emitted by the electron beam emitter 1 can be introduced completely into the reflector apparatus 4, so that no electron beams 2 can escape to the external environment A and are thus no longer available for the sterilization of the interior space I of the pre-form 3.

As a result of this, the reflector apparatus 4 also has a third portion 4f which is arranged substantially between the first portion 4d and the second portion 4e and which has a diameter which is reduced substantially continuously in the longitudinal direction L of the reflector apparatus 4, as viewed in the direction of the first portion 4d starting from the second portion 4e.

Figure 3:
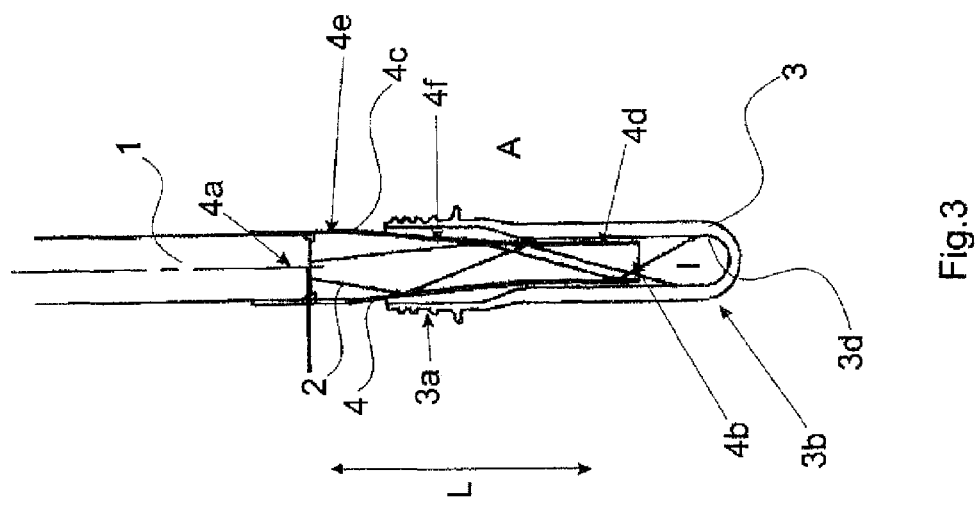
FIG. 3 is a basic drawing of an embodiment of a reflector apparatus of the apparatus according to the invention for the sterilization of an interior space of containers according to FIG. 2 in a position situated at least in part in the interior space of an embodiment of a pre-form.

FIG. 3 is a basic drawing of an embodiment of a reflector apparatus 4 of the apparatus according to the invention for the sterilization of an interior space I of containers 3 according to FIG. 2 in a position situated at least in part in the interior space I of an embodiment of a pre-form 3.

Consequently the reflector apparatus 4 and/or also the pre-form 3 has or have been moved substantially in the longitudinal direction L by means of a reciprocating device (not shown here) in such a way that within a defined or pre-set period of time the reflector apparatus 4 is introduced at least with the first portion 4d substantially continuously into the interior space I of the pre-form.

This means that a relative movement preferably takes place between the reflector apparatus 4 and the pre-form 3, during which either the reflector apparatus 4 is moved to the pre-form 3 or the pre-form 3 is moved to the reflector apparatus 4. It is also possible, however, for both the reflector apparatus 4 and the pre-form 3 to be moved to each other by means of the reciprocating device, so that at least the first portion 4d of the reflector apparatus 4 can be introduced substantially stepwise into the interior space I of the pre-form 3.

During the procedure of the substantially continuous introduction or insertion of the at least first portion 4d of the reflector apparatus 4 into the interior space I of the pre-form 3, electron beams 2 are emitted by the electron beam emitter 1, are introduced into the reflector apparatus 4, are reflected and preferably also bundled in the latter, and are applied in the form of reflected and bundled beams 2 to the internal surface 3d of the pre-form 3.

In addition, it is possible for electron beams 2 to continue to be applied to the internal surface 3d of the pre-form for the sterilization thereof during the withdrawal of the at least one first portion 4d of the reflector apparatus 4 out of the interior space I of the pre-form 3, so that a sterilization of the interior space I of the pre-form 3 preferably takes place during the entire relative movement of the reflector apparatus 4 or the pre-form 3 respectively and, in particular, directly after the entry of the reflector apparatus 4 into the aperture area 3a of pre-form 3.

The Applicants reserve the right to claim all the features disclosed in the application documents as being essential to the invention, insofar as they are novel either individually or in combination as compared with the prior art.

LIST OF REFERENCES 1 electron beam emitter
1a outlet window
2 electron beams
3 pre-form
3a aperture area
3b lower/distal end
3c wall
3d internal surface/inner wall
4 reflector apparatus
4a first opening
4b second opening
4c internal surface
4d first portion
4e second portion
4f third portion
A external environment
D3a diameter in the aperture area
D3b diameter in the lower area
I interior space
L longitudinal direction

The invention claimed is:

1. An apparatus for the sterilization of inner walls of containers with at least one electron beam emitter with at least one electron beam accelerator and with an outlet window for the electron beams, a conveying device for conveying the containers to be sterilized and a reciprocating device for creating a relative movement between the containers and the outlet window in a longitudinal direction (L) of the containers, wherein a reflector apparatus is connected to the electron beam emitter in a positively locking and/or friction locking manner at least locally in a region of the outlet window and is arranged to be introduced at least locally during a defined period of time into an interior space (I) of the container to be sterilized, in order to apply the electron beams to the inner walls of the container.

2. The apparatus according to claim 1, wherein the reflector apparatus is in the form of a tube and has at least one first opening for the admittance of the electron beams into the reflector apparatus and one second opening for the exit of the electron beams into the interior space (I) of the containers to be sterilized as well as an internal surface for reflecting and/or bundling the electron beams.

3. The apparatus according to claim 2, wherein at least the internal surface of the reflector apparatus has at least in part a material with a large nucleus mass.

4. The apparatus according to claim 3, wherein the material is selected from the group consisting of tungsten, tantalum, platinum, gold and/or materials with comparable chemical and physical properties.

5. The apparatus according to claim 2, wherein a cross section of the second opening is smaller than a cross section of the first opening.

6. The apparatus according to claim 1, wherein at least one first portion of the reflector apparatus has a smaller diameter than a second portion of the reflector apparatus, which is connected to the electron beam emitter.

7. The apparatus according to claim 6, wherein at least one third portion of the reflector apparatus, as viewed in the direction of the first portion starting from the second portion, has a region which tapers in diameter.

8. The apparatus according to claim 1, wherein the reflector apparatus is used for guiding a tempering air flow for tempering the container during the sterilization procedure.

9. The apparatus according to claim 1, wherein the reflector apparatus is connected to the electron beam emitter in a detachable manner.

10. The apparatus according to claim 1, wherein the reflector apparatus is suitable for guiding a tempering air flow for tempering the container.

11. The apparatus according to claim 1, wherein the apparatus includes a vacuum chamber.

12. The apparatus according to claim 1, wherein the outlet window comprises a metallic foil.

13. The apparatus according to claim 12, wherein the metallic foil of the outlet window is formed of titanium.

14. The apparatus according to claim 1, wherein the reflector apparatus has a circular cross section.

15. The apparatus according to claim 1, wherein the outlet window has a diameter which is larger than the diameter of the interior space of the container to be sterilized.

16. The apparatus according to claim 1, wherein the apparatus further comprises a reciprocating device which moves the beam emitter in the direction of the container to be sterilised.

17. A method of sterilizing inner walls of a container using electron beams discharged by an electron beam emitter, wherein a reflector apparatus, connected in a region of an outlet window of the electron beams in a positively locking and/or friction locking manner to the electron beam emitter, for reflecting and/or bundling the electron beams, is introduced at least locally during a defined period of time into an interior space (I) of the container to be sterilized, in order to apply the electron beams to the inner walls of the container.

18. The method according to claim 17, wherein the reflector apparatus reflects at least one of the electron beams emitted by the electron beam emitter at least once after the exit thereof out of the electron beam emitter by way of an internal surface having at least in part a material with a large nucleus mass.

19. The method according to claim 17, wherein the interior space (I) of pre-forms is sterilized by the reflector apparatus by the application of electron beams reflected and bundled on an internal surface of the reflector apparatus.

20. The method according to claim 17, wherein the reflector apparatus and/or the containers is or are moved during a defined period of time at least for a time at a relative movement velocity in a longitudinal direction (L) of the containers by a reciprocating device in order to permit a relative movement between the containers and the reflector apparatus.

21. The method according to claim 17, wherein the containers are plastics preforms.

22. The method according to claim 17, wherein a tempering air flow is used for cooling a foil of the electron outlet window.

* * * * *